United States Patent [19]

Zambelli et al.

[11] 3,977,081
[45] Aug. 31, 1976

[54] RIGID IMPLANTATIONS FOR SURGICAL PURPOSES

[75] Inventors: Celestino Zambelli, Milan; Fiorino Pagani, Lucca, both of Italy

[73] Assignee: Bioimplant S.a.s. di Fiorino Pagani & C., Lucca, Italy

[22] Filed: Mar. 4, 1975

[21] Appl. No.: 555,300

Related U.S. Application Data

[63] Continuation-in-part of Ser. No. 453,006, March 19, 1974, abandoned.

[30] Foreign Application Priority Data

Mar. 22, 1973  Italy .................................. 21974/73

[52] U.S. Cl. ............................................. 32/10 A
[51] Int. Cl.² ........................................ A61C 9/00
[58] Field of Search .................... 32/10 A, 10 R; 128/92 C

[56] References Cited
UNITED STATES PATENTS

| | | | |
|---|---|---|---|
| 1,140,538 | 5/1915 | Skinner | 32/10 A |
| 3,435,526 | 4/1969 | Brancato | 32/10 A |
| 3,499,222 | 3/1970 | Lenkow et al. | 32/10 A |
| 3,579,829 | 5/1971 | Sampson | 32/10 A |
| 3,748,739 | 7/1973 | Thibent | 32/10 A |
| 3,837,080 | 9/1974 | Pasqualini | 32/10 A |

*Primary Examiner*—Jack Q. Lever
*Attorney, Agent, or Firm*—Haseltine, Lake & Waters

[57] ABSTRACT

Implants for dental use having, in addition to a high mechanical strength, also a high dielectricity providing a high resistance to electrochemical and chemical attack. A rigid implantation for dental uses comprises a metal core totally covered with a firmly adhering layer of tetrafluoroethylene or polymers thereof, this metal core being shaped so that a portion thereof is designed to be and remain endosseous and a portion thereof is designed to be and remain juxtaosseous, the implantation having rounded edges.

5 Claims, 7 Drawing Figures

RIGID IMPLANTATIONS FOR SURGICAL PURPOSES

CROSS RELATED APPLICATION

This application is a continuation-in-part application of Ser. No. 453,006; filed Mar. 19, 1974 and now abandoned.

FIELD OF THE INVENTION

The present invention relates to rigid implantations for surgical purposes, particularly as may be partially or fully inserted in a human organism.

DISCUSSION OF THE PRIOR ART

It is known that metal prostheses are widely utilized for making rigid implantations for surgical purposes, particularly in the dental field. For example, for the support of teeth, dental bridges or complete dentures, recourse is had to rigid elements in the form of screws, wickers, needles, blades, grates and the like, which are driven into suitable seats, previously formed in the maxilla or jaw bones.

These rigid elements are normally made of expensive and difficultly machinable noble metals. However, the rigid metal implantations suffer from the serious disadvantage of being subjected, after surgical implantation thereof into a human organism, to corrosions and thus to a degradation, particularly as a consequence of attack by ions of different nature and, more generally, as a result of electric attack caused by electrochemical and piezoelectric phenomena (the latter resulting from the microcrystalline nature of the bone salt).

For example, the rigid elements (wickers, screws, blades, etc.) as required for the support of teeth are usually made of titanium, which is a metal exhibiting excellent characteristics from the standpoint of chemical and mechanical strength.

However, it is known that such rigid elements, when implanted in a patient's mouth, come into contact with the saliva, which at times may have either acid or basic properties. It is also known that titanium is attacked by a number of chemicals, such as hydrochloric acid, oxalic acid, formic acid, sulphuric acid, and particularly hydrofluoric acid. There are also dental implantations in which variations in pH are generated adjacent to the implantations.

Keeping in mind that a dental prosthesis could and should be able to remain in situ over a very large number of years, it will be understood that, over the long run, there may take place a chemical corrosion of the metal elements, particularly titanium elements, which have the teeth fastened thereto.

Furthermore, it is also known that prostheses constituted of metals other than the metal used for supporting a given tooth, may be present in a patient's mouth.

The presence of such different metals may give rise to formation of galvanic couples which may cause annoying sensations to the patient, and above all may lead to an electrochemical corrosion of the tooth supporting element. For example, it is known that titanium and alloys thereof form galvanic couples with copper and nickel alloys, and particularly with stainless steels.

While still considering titanium prosthesis, which are those most widely used due to the inherent strength and lightness thereof, and because of absence of any rejection phenomena after implantation thereof, in addition to the disadvantages of some slow chemical, electrochemical and electric corrosion taking place due to piezo-electric phenomena caused by bone salt, it has been ascertained that no epithelial adhesion (i.e. no adhesion of mouth mucosa) occurs by this metal with the collar of the rigid elements used as tooth support, while providing a good ossification all about the elements. This results in the occurrence of aesthetic problems of quite a difficult solution.

In order to overcome the above-mentioned disadvantages, such implantations have been provided which comprise a metal core covered with a plastics material layer which appears to perform the dual function of enabling the use of a core made of any metal, as an integral or welded element, and avoiding all of the shortcomings resulting from the presence of metals contacting organic tissues.

However, all of the plastic materials, as presently known, with or without additives of any nature, are liable to become impregnated with organic liquids which give rise to cytotoxicity within the plastic material. That type of material may be found, for example, in the disclosure of Hodosh U.S. Pat. No. 3,790,507. Discussion of plastic-coated metal implants may also be ascertained from the Journal of Biomedical Materials Research, Vol. 6, No. 5, September 1972 pp. 451–464, in an article by C. A. Homsey et al. "Reduction of Tissue and Bone Adhesion to Cobalt Alloy Fixation Appliances."

The only synthetic material not liable to impregnation is tetrafluoroethylene and polymers thereof, this material being commonly known under the registered trademarks TEFLON, FLUON, ALGOFLON or the like, which, as is well known, is widely used in the surgical field.

Recently, use has also been proposed of dental implantations comprising a metal core covered with tetrafluoroethylene. Such an implantation is described in Linkow et al. U.S. Pat. No. 3,499,222. However, it should be noted that such implantations, as known in the art, are endosseous, that is the resistant structure which is to withstand the mechanical stresses (consider, for example, that in the case of mastication, the pressure exerted on a molar is in the order of 60 kg/sq. cm.) is totally embedded in the bone.

Completely juxtaosseous metal implantations are also known, which implantations have a rigid carrying structure bearing on the osseous lamina of jaws with stumps for tooth fastening. Such metal implantations have the merit of satisfactorily withstanding even high pressures, but suffer from the serious disadvantage of having poor stability and exposing the mucosa instead of being covered thereby. No description is found in literature that such implants can be covered with tetrafluoroethylene, but even in such a case, they would still have poor stability after implantation thereof.

Finally, it should be noted that endosseous implants have sharp edges or tips which appear to perform the function of facilitating the insertion into the osseous seats, but suffer from the drawback that, being covered with fibromucosa after insertion in the osseous seat, they form sources for causing suffering or discomfort, and inflammation of the mucosa.

SUMMARY OF THE INVENTION

Accordingly, it is an object of the present invention to provide implants for dental use having, in addition to a high mechanical strength, also a high dielectricity providing a high resistance to electrochemical and chemical attack.

This and further objects are attained by a rigid implantation for dental uses comprising a metal core totally covered with a firmly adhering layer of tetrafluoroethylene or polymers thereof, this metal core being shaped so that a portion thereof is designed to be and remain endosseous and a portion thereof is designed to be and remain juxtaosseous, the implantation having rounded edges.

BRIEF DESCRIPTION OF THE DRAWINGS

For a clearer understanding of the structure and features of the implantation according to the present invention, reference may now be had to various embodiments of the invention, described in connection with the accompanying drawings, in which.

DETAILED DESCRIPTION

Figure 1:
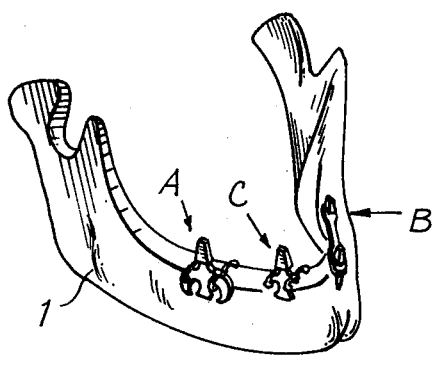
FIG. 1 schematically shows a jaw bone to which there have been applied implantations of different types.

Referring first to FIG. 1, a jaw bone is schematically shown as carrying three different types of implants, designated by letters A, B and C, respectively.

Figure 2:
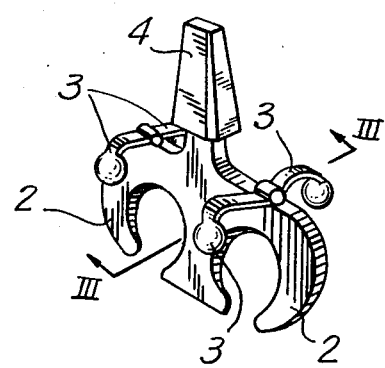
FIG. 2 is a perspective view showing an embodiment of the endosseous blade for tooth support.
Figure 3:
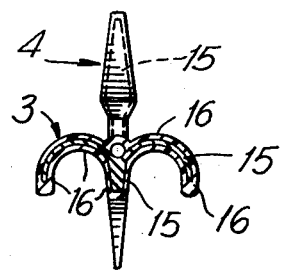
FIG. 3 is a cross-section of the blade taken along line III—III in FIG. 2.

Implant A is shown in a perspective view in FIG. 2 and in a sectional view in FIG. 3, and comprises an endosseous blade 2 and two pairs of arms 3 projecting from either side of blade 2. These arms 3 are for the juxtaosseous bearing of the implant and are spaced apart through a stump or base 4 intended to project into the oral cavity and to operate as a tooth support.

As shown in FIG. 3, the whole implant comprises a metal core 15 which is completely covered with a firmly adhering layer 16 of tetrafluoroethylene or polymers thereof.

As shown particularly in FIG. 2, the free ends of arm 3 have enlargements performing the function of increasing the bearing surface of the arms acting on the bone. Arms 3 are of flattened shape with somewhat rounded edges, and blade 2 as well has a flattened shape with rounded edges.

The method by which the metal core is covered with a firmly adhering layer of tetrafluoroethylene is already known in the art and the thickness of the layer of the polytetrafluoroethylene film may normally be within the range of 30–50 microns.

The rigid implantation of FIGS. 2 and 3 is applied to a jaw bone by milling a bore therein and driving the endosseous blade 2 into the bore, while arms 3 bear on or slightly insert into the osseous lamina of the jaw bone, but still remaining externally thereof. When the tooth has been fastened on stump or base 4, arms 3 perform the function of withstanding compressive stresses, whereas blade 2 has the main function of ensuring the implant retention.

Because of its partially endosseous and partially juxtaosseous structure, and due to the fact that the whole implantation is covered with tetrafluoroethylene and no cutting edges or tips are provided, it has been found that such an implantation exhibits optimum stability, is free of any rejection phenomena and that the juxtaosseous arms remain covered with mucosa even a long time after implant installation.

Figure 4:
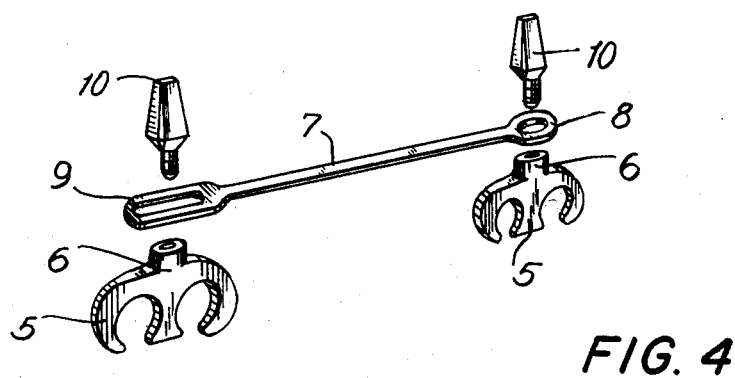
FIG. 4 is a perspective view of an implantation formed of two distinct blades rigidly interconnected by a rigid juxtaosseous structure.
Figure 5:
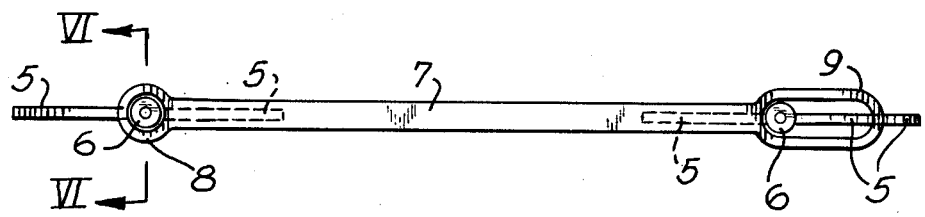
FIG. 5 is a plan view showing the two blades of FIG. 4 as interconnected by the rigid element.
Figure 6:
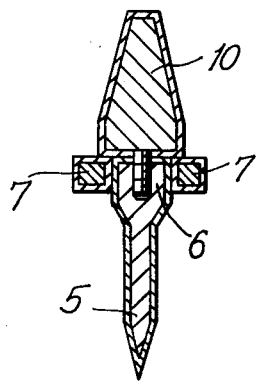
FIG. 6 is a sectional view of the implantation shown in FIG. 5, taken along line VI—VI in FIG. 5.

Reference is now made to FIGS. 4, 5 and 6 relating to the rigid implantation designated by letter B in FIG. 1. This type of implantation is particularly used for tooth fastening on a maxilla which is totally devoid of teeth. This implantation comprises two separate blades 5, the central upper end of which has a polygonal projection 6, wherein a threaded hole is formed, as shown in FIG. 4. The entire blade is made of a metal core which is completely covered with polytetrafluoroethylene, similarly as above set forth in connection with FIG. 2. The implantation also comprises a juxtaosseous connecting bar 7, the shape of which is considerably extended and flattened, and is provided at its ends with, respectively, two enlargements 8 and 9. A polygonal hole is formed in enlargement 8, so that projection 6 of one of the blades 5 can penetrate and be exactly accomodated therein, whereas an extended hole of substantially rectangular cross-section is formed in enlargement 9, so that one of the projections 6 can be accomodated therein, which latter projection is longitudinally movable within the hole of enlargement 9.

Further, bar 7 is made of resistant metal and completely covered with tetrafluoroethylene. In order to assemble the described implantation, two different millings or borings of the bone are provided for, such bores accomodating the endosseous blades 5. Bar 7 is positioned above the blades, so that the hole of enlargement 8 is aligned over the projection 6 of one of the two blades, whereas the other projection 6 of the other of the blades is caused to penetrate the extended hole of enlargement 9. Bar 7 is blocked on the two blades by threaded stumps 10 which are screwed down into threaded holes formed in the projections or extensions 6.

Blades 5 are for implantation retention, while bar 7 directly bearing on the osseous lamina, assures compressive strength. Obviously, bar 7 may be of different lengths depending on the implantation structure or anatomic requirement.

Figure 7:
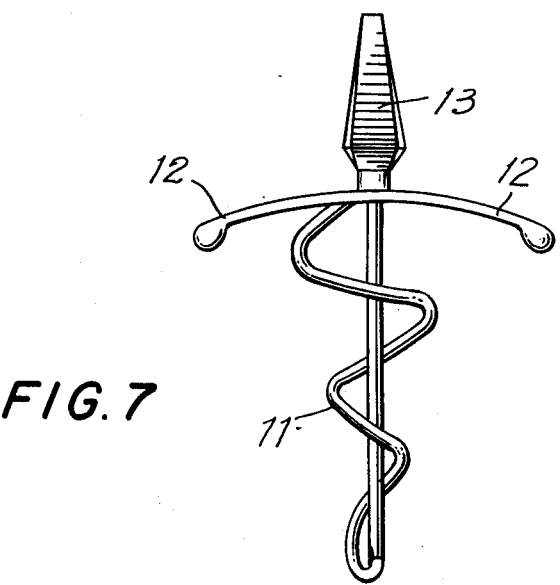
FIG. 7 is a schematic view showing an implantation for a tooth support, formed of a wicker and a rigid juxtaosseous structure.

Referring now to FIG. 7 an implantation designated by C in FIG. 1 is shown, as being suitably accomodated within an alveolus or tooth-socket from which a tooth has just been extracted. This implantation comprises a wicker 11 of a conical spiral shape having two arms 12 and a stump 13 fast therewith, the spiral 11 being adapted for accomodation within the alveolus or tooth-socket and for being effective as the endosseous retention portion of the implantation, while arms 12 are adapted to operate as juxtaosseous portions for withstanding the compressive stresses, stump or base 13 being adapted, as is usual, to directly support or carry a tooth.

While the metal core forming part of the implantations can be constituted of any kind or nature, particularly of low cost metals, the covering of the core, as provided for by the layer of tetrafluoroethylene or polymers thereof (in case a primer layer can be interposed between the metal and tetrafluoroethylene layer), in addition to the advantage of avoiding any risk of rejection, also has the advantage of even assuring an optimum epithelial adhesion to the stump base, the latter of which is part of such implantations and surrounded by the mucosa.

Finally, the surprising novel features of the implantation according to the present invention result from the combination of an assembly of distinct features, i.e. each of the implantations comprises an endosseous portion and a juxtaosseous portion which are firmly restrained to each other, while the whole implantation comprises a metal core having a substantial rigidity and being covered with a layer of tetrafluoroethylene avoiding all of the piezoelectric drawbacks, and is resistant to chemical and electrical attacks while furthermore enabling an optimum epithelial adhesion of both the previously existing mucosa and fibromucosa to be generated about the implantation. Moreover, the implantation is rendered more easily endurable by the complete absence of cutting edges and tips.

While there has been shown what is considered to be the preferred embodiment of the invention, it will be obvious that modifications may be made which come within the scope of the disclosure of the specification.

What is claimed is:

1. A rigid implantation for dental uses, comprising a metal core completely covered with a firmly adhering layer of tetrafluoroethylene or polymers thereof, including a tooth supporting stump, an elongated endosseous portion supporting said stump and having means for implantation in the jawbone of a patient and a juxtaosseous portion located between said stump and said endosseous portion with means for externally bearing on said jawbone of the patient, the implantation having rounded edges.

2. An implantation as claimed in claim 1, wherein said juxtaosseous portion comprises at least two flattened arms projecting from the endosseous portion.

3. An implantation as claimed in claim 2, wherein said flattened arms are firmly secured to said endosseous portion and spaced apart from said tooth-supporting stump.

4. An implantation as claimed in claim 1, wherein said endosseous portion comprises two separate blades and said juxtaosseous portion comprises a rigid bar having enlarged ends provided with holes, said blades including respective extensions projecting therefrom through said holes in said bar, and threaded tooth-supporting stumps fastened to said blades.

5. An implantation as claimed in claim 4, wherein said extensions have threaded holes receiving said threaded tooth-supporting stumps.

* * * * *